United States Patent [19]

Munson et al.

[11] Patent Number: 5,571,522
[45] Date of Patent: Nov. 5, 1996

[54] BAIT WITH CORN GERM

[75] Inventors: Derrill Munson, Pittsboro, N.C.; Chel W. Lew, San Antonio, Tex.; James M. Gaggero, Citrus Heights, Calif.; Keith Branly, Brandon, Fla.

[73] Assignee: Micro Flo Company, Mulberry, Fla.

[21] Appl. No.: 189,355

[22] Filed: Jan. 31, 1994

[51] Int. Cl.⁶ ........................................... A01N 25/14
[52] U.S. Cl. ..................... 424/410; 424/84; 424/405; 424/407; 424/492; 424/499; 424/195.1
[58] Field of Search .................... 424/408, 409, 424/405–407, 410, 418, 492, 499, 84; 514/195.1

[56] References Cited

U.S. PATENT DOCUMENTS

| | | | |
|---|---|---|---|
| 2,687,365 | 8/1954 | Link | 424/410 |
| 2,770,067 | 11/1956 | Lindblom | 43/124 |
| 3,252,785 | 5/1966 | Hoblit | 71/23 |
| 3,272,696 | 9/1966 | O'Connell | 167/30 |
| 3,272,698 | 9/1966 | Lemin et al. | 167/30 |
| 3,496,272 | 2/1970 | Kruger | 424/238 |
| 4,049,460 | 9/1977 | Broadbent | 106/15 R |
| 4,238,484 | 12/1980 | Stein et al. | 424/202 |
| 4,320,130 | 3/1982 | Balsley et al. | 424/251 |
| 4,440,746 | 4/1984 | Maglio | 424/78 |
| 4,764,372 | 8/1988 | Hewnstadt | 424/93 |
| 4,815,923 | 3/1989 | Lush | 424/410 |
| 4,834,977 | 5/1989 | Kohama et al. | 424/405 |
| 4,985,413 | 1/1991 | Kohama et al. | 574/79 |
| 4,992,275 | 2/1991 | Lush | 424/408 |
| 5,244,669 | 9/1993 | Satom et al. | 424/438 |

FOREIGN PATENT DOCUMENTS

| | | | |
|---|---|---|---|
| 1195922 | 10/1985 | Canada. | |
| 0228228 | 8/1987 | European Pat. Off.. | |
| 5615204 | 7/1979 | Japan | 424/84 |
| 59-6720908 | 8/1982 | Japan. | |
| US85-00405 | 9/1985 | WIPO. | |

*Primary Examiner*—Neil S. Levy
*Attorney, Agent, or Firm*—Banner & Allegretti, Ltd.

[57] ABSTRACT

Baits useful against diabroticine mature and immature beetles contain (a) an insecticide and (b) a feeding stimulant containing corn germ.

14 Claims, No Drawings

BAIT WITH CORN GERM

FIELD OF THE INVENTION

The invention relates to a bait having a particularly effective form and structure for control of various insects and particularly for immature and adult diabroticine beetles.

BACKGROUND OF THE TECHNOLOGY

Diabroticine beetles are a significant problem during the growth of, inter alia, corn (field, pop, seed, and sweet), beans, Cucurbitaceae (including cucumbers, melons, squash, and pumpkins), peanuts, peas, potatoes, and sweet potatoes. Corn is conveniently used to describe the effects of diabroticine beetles. These pests are the direct or indirect (i.e., as a vector for bacteria and inoculation of melons and squash) cause of millions of dollars of crop and garden damage annually. Damage by these beetles has continued despite over 30 years of attempts at control.

Diabroticine beetles encompass multivoltine and univoltinc species. Multivoltine species (e.g., the southern corn rootworm) can produce up to 3 generations a year. Univoltine species (e.g., northern and western corn rootworm) have a life cycle that starts with eggs laid 4–24 inches below the soil surface in the fall. In early spring and over the course of several weeks, the larvae (a form of immature beetle) hatch and begin to feed on nearby roots thereby destroying the root's anchoring abilities and the microhairs responsible for mineral, nutrients, and water assimilation. If the plant roots have not been so damaged that the plants falls over, the yield from the affected plants is reduced due to impaired nutrition.

After feeding, the diabroticine larvae pupate and emerge from the ground as adult beetles. Univoltine beetles emerge at some time during mid July through August (depending on local climate). Male diabroticine beetles emerge about 1 week before the females (week 1) which, in turn, emerge at about the same time as corn silks emerge. Because the fresh silks emit a number of volatile agents which are attractive to both the male and female beetles, the 7–10 days of silking represents a period of high feeding activity for the beetles. The beetles immediately begin to migrate up the stalk toward the leaves, ears, and silks. This compulsion is quite strong since there is evidence that the beetles will not move down the corn stalk in response to attractants. Throughout this period, the beetles feed and mate.

The key to control of the diabroticine beetles is to disrupt the life cycle by affecting the immature and/or adult beetles. One method known in the art as "banding" refers to the practice of trying to control the larvae by applying a contact insecticide in or along a furrow containing planted seeds. The theory behind banding is that larvae will enter the treated area when searching for roots and die due to contact with the insecticide.

Unfortunately, microbial attack impairs the efficacy of insecticides in the soil well before all the larvae have had time to hatch and enter the treated band. Concerns for groundwater contamination, the impact on nontarget organisms (e.g., bird kill), and the hazards of human exposure to the toxic insecticides all restrict the use of soil insecticides that might be capable of surviving in the soil through the larval feeding stage.

The effectiveness of banding is also limited by the plants themselves. Plant roots often extend well beyond the treated band leaving the roots vulnerable to attack.

It has been proposed to use the tissue of dried gourds from the Cucurbitale order in combination with 0.01–10% by weight (wt %) of an insecticide to make a lethal bait for the control of diabroticine beetles. Due to genetic evolution, corn rootworm larvae have evolved to compulsively feed on cucurbitacins.

From Canadian Patent No. 1,195,922, the bitter tasting cucurbitacins in the gourd tissue acts as a compulsive feeding stimulant for diabroticine beetles but does not harm beneficial insects. By coating the gourd tissues with an insecticide, it was intended that the beetles would compulsively consume a lethal quantity of insecticide.

Unfortunately, it is difficult and expensive to grow cucurbitale order crops with high cucurbitacin concentrations. Hybrid species must be located or selected to provide even a marginal level of cucurbitacins.

Also proposed in Lush U.S. Pat. No. 4,992,275 is the use of 3–6 mm pellets containing an active insecticide and whole, dried, ground, raw sweet corn. The bait is taught as useful for controlling corn rootworm larvae as well as cutworms, wireworms, billbugs, seed corn maggots, grubs, lesser corn stalk borer, seed corn beetle, flea beetles, European and Southwestern corn borer, fire ants and other ant species, onion maggots, sweet potato weevils, and root maggots, among other types of chewing insects that feed on a variety of plants. Although it is broadly disclosed that "binders for holding the bait particles together" (column 2, lines 3–4) may be used, other passages teach that natural sweet corn is sufficiently high in oil and sugar that added oils and sugars are unnecessary (column 7, lines 20–27). In addition, rain or winds is taught to remove the bait from the treated zone necessitating retreatment (column 4, lines 33–36).

It would be desirable to have a bait formulation that used safe, inexpensive ingredients with a high level of efficacy against immature and mature diabroticine even when applied through conventional spraying equipment in aqueous solution as well as when applied as a dry granular bait.

SUMMARY OF THE INVENTION

It is an objective of the invention to provide a bait and method of use thereof having high levels of pest control and which is particularly effective against diabroticine populations.

It is another objective of the invention to provide a composition containing an intimate admixture of a feeding stimulant and insecticide in a form useful for application as a dry granular solid or as a solid suspended in aqueous solution using conventional spraying equipment.

In accordance with these and other objectives that will become apparent from the description herein, baits according to the invention comprise particulate composite baits comprising a binding agent in which is homogeneously dispersed a mixture of (a) 0.01–99 wt % of diabroticidal insecticide; and (b) 0.01–99 wt % of a feeding stimulant comprising corn germ and less than 25 wt % corn endosperm associated therewith.

The present bait provides a physical form with high efficacy. The homogeneous distribution assures that consumption of a corn germ particle will also include consumption of an adjacent insecticide particle. Corn germ is also inexpensive and readily grown in a variety of climates. The bait exhibits a high rate of kill in targeted immature as well as mature diabroticine beetles at low material application rates.

DETAILED DESCRIPTION

The present invention provides corn germ as a diabroticine feeding stimulant homogeneously dispersed with an insecticide in a binder matrix. Depending on the binder selected and the diameter of the bait, the bait can be applied in the form of a dry granular or a bait sprayed through conventional spraying equipment.

CORN GERM FEEDING STIMULANT

Corn germ is the diabroticine insect feeding stimulant component for baits of the invention. Corn germ is made of the embryo and scutellum portions of a corn seed which are usually separated from the starch endosperm during milling. Corn germ is a commercial by-product from the production of corn oil. Until the present invention, corn germ has been used for animal food.

The corn germ component of the bait is used in an amount sufficient to stimulate feeding in target insects. In general, baits can contain corn germ in an amount within the range of 0.01–99 wt % based on the total weight of the bait and insecticide within the range of 0.01–99 wt % based on the total weight of the base. Preferably, the baits contains at least 15 wt % corn germ. Even more preferably, the baits contain about 30–90 wt % corn germ.

According to the present invention, it is only the germ portion of the corn that acts as a feeding stimulant. Any of the starchy corn endosperm that is associated with the corn germ in the baits should be in minor amounts that may be incidentally produced in the commercial separation of corn germ from the whole corn kernel. Generally, the amount of incidental endosperm associated with the corn germ and as found in the baits is less than 25 wt %, preferably less than 20 wt %, and even more preferably less than about 15 wt % based on the weight of the corn germ. Such amounts do not materially affect the feeding stimulation effect for baits of the invention.

There is no need or desire to employ whole kernel baits as in Lindblom U.S. Pat. No. 2,770,067 or ground whole kernels as in Lush U.S. Pat. No. 4,992,275 due to the added expense and dilution effect on the feeding stimulant effects in the bait. In addition, the use of unnecessary starch from the endosperm could interfere with conventional spraying equipment due to thickening of the spray solution in the tank.

INSECTICIDES

Insecticides useful for the invention are those effective to control the insect populations by killing or sterilizing the immature or adult beetles. Generally, an amount within the range of 0.01–99 wt %, preferably 0.1–50 wt %, even more preferably an amount within the range of 0.01–25 wt %. A particularly preferred amount of insecticide is within the range from about 5–25 wt % based on the total weight of the bait.

Insecticides useful in the invention are materials and biological agents that control diabroticine populations through lethal ingestion, sterilization, or other interference with the diabroticine life cycle. Exemplary insecticides include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, and phosmet); compounds which break down the beetle's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); *Bacillus thuringiensis*; and diabroticidal viruses (e.g., entomopathic viruses such as the bacculo viruses).

Most insecticides are commercially available in the form of a solid particle. Liquids may be used in the baits homogeneously mixed with the binder. The use of microencapsulated liquids or fine solids that become intimately bound with corn germ are preferred for handling and control. In general, phorate and the carbamates are preferred with phorate, carbaryl and methomyl being most preferred.

The present invention provides a method of using the baits to control insect infestations in a variety of plants. It should be noted that the term "insect" is used herein to denote the control of either immature or adult stages or both immature and adult stages so long as either form consumes solid food for sustenance and growth. In some multivoltine insect species exhibiting overlapping generations, application of the present baits can be used to control both adults and immature forms thereof simultaneously.

Insects that can be controlled with the present invention include insects of the diabroticine genus as well as cutworms, wireworms, billbugs, seed corn maggots, grubs, lesser corn stalk borer, seed corn beetle, flea beetles, European and Southwestern corn borer, fire ants and other ant species, onion maggots, sweet potato weevils, root maggots, and other types of chewing insects that feed on a variety of plants.

Specific diabroticine insects that are advantageously controlled in accordance with the invention include the banded cucumber beetle (*Diabrotica balteata*), the green maize beetle (*Diabrotica decolor*), the twelve-spotted cucumber beetle (*Diabrotica duodecimpunctata*), the northern corn rootworm (*Diabrotica barberi*), the southern corn rootworm or spotted cucumber beetle (*Diabrotica undecimpunctata howardi*), the western spotted cucumber beetle (*Diabrotica undecimpunctata undecimpunctata*), the western corn rootworm (*Diabrotica virgifera virgifera*), the striped cucumber beetle (*Acalymma vittata*), Western striped cucumber beetle (*Acalymma trivittata*), the Mexican corn rootworm (*Diabrotica virgifera zeae*), *Diabrotica adelpha, D. speciosa speciosa, D. speciosa vigens, D. viridula, D. cristata, D. undecimpunctata sensulato, D. undecimpunctata tenella,* and *D. undecitnpunctata duodecimnotata*.

BINDERS

Binders for the present bait include materials and amounts thereof that are palatable to diabroticine insects that are able to bind together the insecticide and corn germ components yet pass through extruders, sprayers, and agglomeraters conventionally used to form particles. Suitable binders include hot water soluble polymers (e.g., pork or beef gelatin, xanthan gum, carrageenan, guar gum, gellan gum, agar and gum karaya), water soluble polymers (e.g., polyethylene glycol), water swellable polymers (e.g., polyethylene glycol containing zein, shellac, or a fatty acid amide in an amount sufficient to reduce the water solubility), sodium alginate that is later crosslinked with soluble calcium, and mixtures thereof.

Binders can be used in an amount within the range from about 1 wt % to about 95 wt % in a quantity sufficient to bind together the insecticide and corn germ in a structurally sound bait. Preferably, the binder is used in an amount of about 1 wt % to about 50 wt % and more preferably within the range from about 1–35 wt % based on the total weight of the bait. A particularly preferred amount of gelatin as the binder is within the range from about 5–30 wt % based on the total bait weight.

For sprayed baits, the binder material should have a low solubility in cold water to ensure that the bait components are not released in the spray tank or cause undesired drift after passing through the spray nozzle. General, the binder for a sprayed bait should exhibit a solubility in cold water that is less than about 5% by weight, preferably less than about 2 wt %, and most preferably less than about 1 wt %.

High bloom gelatin (i.e., 200–300) is a particularly preferred binder that provides hydratable solids which, in a sprayed bait, cause the bait to exhibit a gumdrop-like, chewable consistency for an extended period of time. Importantly, the gelatin binder will hydrate and soften without dissolving significantly or releasing the bound feeding stimulant and insecticide despite the application of the type of shear forces found in commercial spraying apparatus. The gelatin also exhibits good wetting and suspension in spray tanks.

If intended for application through conventional spraying equipment, the baits are desirably formed into a roughly spherical bait having a diameter of less than about 1000 μm. Preferably, 100% of the bait exhibits a particle size within the range from about 100 μm to about 600 μm. Particularly effective particle sizes are when 100% of the bait particles are within the range of about 300 μm to about 600 μm. For homogeneously formed particles within these ranges, consumption of the feeding stimulant will necessarily involve consumption of the insecticide.

Dry granular baits, on the other hand, will generally exhibit a larger corresponding size within the range from about 800 μm to about 2000 μm. Within the range of about 600–800 μm, the baits can be used as either a sprayable bait or a dry granular bait depending on the cold water solubility of the binder employed.

Dry granular baits are desirable made by depositing a homogeneous mixture of corn germ, insecticide, and binder on corn cob grit. Alternatively, a plurality of <600 μm preformed baits, such as those dispersed by spraying, can be deposited on a grit carrier and held thereon with the same binder as in the bait or a different binder.

Plants that can be protected according to the present invention include virtually any plant affected by diabroticine beetles. Examples of such plants include, inter alia, corn (field, pop, seed, and sweet), beans, Cucurbitaceae (including cucumbers, melons, squash, and pumpkins), peanuts, peas, potatoes, and sweet potatoes.

Baits of the invention exhibit a surprisingly high level of diabroticine control while enabling the application of overall lower levels of insecticide relative to conventional practice. For example, the currently approved application rate for control of diabroticine beetles by carbaryl is 454–908 grams active ingredient (AI) carbaryl per acre of treated area. With the present invention, however, the higher levels of control are realized by a significantly lower application rate. For carbaryl, this rate is within the range from about 2 to about 200 g AI/acre, preferably about 5–100 g AI/acre, and most preferably about 20–50 g AI/acre. Practical carbaryl formulations will translate into an application rate of 2–20 lbs. of bait per acre when formed as a dry granule using an inert carrier (such as corn cob grit or clay) or 5–50 ounces of suspended bait per acre.

The quantities of diabroticidal insecticides other than carbaryl are used in quantities proportional to their diabroticidal efficacy relative to the levels of carbaryl used herein. As an example, diabroticidal insecticides that are 50% as effective as carbaryl are used in quantities of 5–400 g AI/acre, but insecticides that are twice as effective are used in quantities within the range from about 1–100 g AI/acre. The precise application rate of any particular insecticide when supplied in baits of the present invention is readily determinable by one in this art with the exercise of no more than the existing skill level after consideration of the present disclosure.

ADDITIVES

A number of additional materials can be included in the baits of the present invention. Plasticizers can be used to enhance the softness of the hydrated bait and wetting in aqueous suspensions. Useful plasticizers include sorbitol, maltodextrin, glycerin, and sucrose in an amount within the range from about 5 wt % to about 20 wt %. Preferably, plasticizer is used in an amount within the range of about 1–10 wt %.

A preservative can be added in an amount sufficient to inhibit or prevent deterioration during storage and transport. Suitable preservatives include a material commercially available under the trademark Proxell™ and sodium benzoate. Suitable amounts of preservatives are within the range from about 0.05 wt % to about 1 wt %, preferably in an amount within the range of about 0.05–0.4 wt %.

Gums are useful in the binder for increasing palatability of the bait to the immature and adult beetles and, when the bait is to be distributed by spraying, as a hydratable solid in addition to gelatin that will swell and maintain a binding effect without dissolving in an aqueous spray medium. Suitable gums for the invention include xanthan gum, carrageenan, and gellan in an amount within the range of 0–10 wt %, preferably, within the range from about 0.01–5 wt %.

Clays can be used to increase the density of the bait particle when bait according to the invention is formed as a dry granular bait that is distributed without spraying. Clay is added to form a bulk bait density within the range of about 25 to about 50 lb/ft$^3$ (400–800 kg/m$^3$), preferably within the range of about 30–40 lb/ft$^3$ (480–640 kg/m$^3$), and even more preferably about 35 lb/ft$^3$ (560 kg/m$^3$). Clays useful in the invention include kaolin, montmorrilonite, attapulgite, and bentonite. Generally, such clays are used as a bait component in an amount within the range from about 5 wt % to about 30 wt %, preferably, about 10 wt % to about 20 wt %.

The baits may also contain one or more attractants for the target insect. Attractants such as those in U.S. Pat. No. 4,880,624 are preferred for diabroticine insects.

Baits according to the invention can also include a nontarget feeding deterrent to deter unintended consumption by birds, mammals, and beneficial insects. Cucurbitacins are advantageously used as the nontarget feeding deterrent because cucurbitacins are feeding stimulants for the target diabroticine insects.

The cucurbitacin can be added to the bait as a dilute cucurbitacin-containing solid or liquid with a concentration of less than about 1 wt % cucurbitacin, as a purified compound, or as a concentrated liquid containing more than about 10 wt % cucurbitacins. The cucurbitacins can be added as discrete particles homogeneously distributed throughout the bait or as a liquid stream that is homogeneously distributed throughout the bait or applied as a surface coating. The cucurbitacin-containing material are preferably added as a discrete plant tissue particles which contain cucurbitacins, cucurbitacin-containing liquids applied to solid carriers such as a corn cob grit, or introduced homogeneously into the matrix with the process liquid used to spray dry the baits. A particularly preferred form for introducing a cucurbitacin component is a concentrated cucrbitacin solution containing 30–50 wt % solids.

References herein the "cucurbitacin-containing" shall mean plant tissue solids and either solid or liquid carriers containing at least one of the cucurbitacins A, B, C, D, E, F, G, H, I, J, K, L, O, P, Q, R aglycone or glycoside terms of any of these. Materials containing cucurbitacins B, D, E, I aglycone or glycoside forms thereof are preferred. A particularly effective bait against diabroticine insects contains a mixture of milled corn germ and cucurbitacins in a weight ratio within the range of about 2:1 to about 5:1, most preferably a weight ratio of about 4:1 corn germ to cucurbitacins.

The present bait can be made by forming a homogeneous mixture of finely divided particles of insecticide and corn germ by many methods such as spray drying, prilling, centrifugal disk, extrusion, agglomeration, or by jet impact between two opposing nozzles. In forming the baits by such method, the individual insecticide and corn germ particles are conveniently less than about 50 μm in diameter with sizes of less than about 25 μm being preferred.

METHOD OF USE

When used as adulticides on diabroticine insects, bait particles of the present invention are applied to the plant surfaces just before emergence of the adult diabroticine beetles or when counts indicate an economic level of infestation. For corn, an economic infestation level for treatment is about 0.5–1 beetles per plant at prevailing crop values and treatment costs. If an economic level of infestation is not seen, commercial fields are not considered to be economically justified for treatment because the losses sustained by beetle damage are worth less than the cost of an average treatment.

An example of treating corn serves as a convenient tool for illustrating the invention. At 7–10 days after first emergence of the adult beetles in corn, the beetle population will be at its peak. Baits of the present invention should on the plants by this time and remain effective for 1—3 weeks to cover overlapping beetle emergence and migration periods. This timing and duration maximize the control over beetles that will produce the progeny causing the succeeding year's root damage.

Dry particles or a liquid suspension of the bait particles are distributed over the tops of the plants to be treated by conventional ground or aerial spraying and equivalent methods with or without herbicides and/or plant nutrients that do not adversely affect the activity of the bait. The objective of such application methods is to deposit bait particles on the upper surfaces of the plant where the diabroticine beetles will locate them while foraging for food.

One method for applying dry bait particles that has proven to be acceptable is to load dry corn cob grit having a size of 10–40 mesh (360–650 μm) with spray dried bait particles according to the invention. These corn cob particles have an open network of pores that will readily hold fine bait particles such as those of the invention yet present a sufficiently large particle size that the grit particles can be applied aerially without experiencing significant amounts of lost material due to bouncing off the plant surfaces upon landing. Preferably, porous carriers for the present bait particles have a bulk density of about that of corn cob grit. In practice, it has been found that the diabroticine beetles will consume bait particles from within the openings of the grit or those that have fallen out as a result of landing on the plant surface. Either mode of consumption results in a high rate of kill.

When used as a larvacide for diabroticine insects at planting, baits are applied to the soil in a furrow containing plant seeds or along at least one of the sides of the seed-containing furrow. Similarly, the baits can be applied post-emergent to or along a furrow containing plants.

When applied to the soil, the bait is applied at a rate corresponding to about 400 grams of active insecticidal ingredient per acre or less. Preferably, the baits are applied in the same manner as the conventional practice of banding at a rate within the range from about 100 to about 200 grams of active diabroticidal insecticide per acre. Immature beetles will feed on the corn germ and, due to the structure of the bait, consume or contact a lethal quantity of the associated insecticide.

EXAMPLES

The following examples are useful to understand the present invention.

EXAMPLES 1–3

Two baits according to the invention were prepared to compare the efficacy of corn germ with buffalo gourd root powder as a source of cucurbitacins on corn rootworm larvae. The feeding response as to each type of bait can be used to compare the effectiveness of corn germ as a feeding stimulant. The formulation of each is presented in Table 1.

TABLE 1

| Component | A (wt %) | B (wt %) |
| --- | --- | --- |
| Gelatin, 300 bloom, type A | 10.0 | 10.0 |
| Kaolin clay | 14.5 | 14.5 |
| Corn germ, milled | 60.0 | 30.0 |
| Buffalo gourd root powder | — | 30.0 |
| Carbaryl technical (99%) | 13.4 | 13.4 |
| Sorbitol | 2.0 | 2.0 |
| Sodium benzoate | 0.1 | 0.1 |

Baits A and B were tested in a 50 mm petri dish with four replications for efficacy in the control of corn rootworm larvae. Blotter paper was cut to fit inside each dish and wetted with 3 ml water. Five mid- to late instar larvae were placed in each dish. Bait exhibited a particle size within the range of 100–355 microns and 25 mg of each was placed in a single spot on the blotter paper. Mortality was measured at 24 and 48 hrs. The results are reported in Table 2.

TABLE 2

| Sample | | Example 1 | Example 2 | Example 3 | Average |
| --- | --- | --- | --- | --- | --- |
| A | (24 hrs.) | 4.75 | 3.5 | 4.75 | 4.33 |
| B | (24 hrs.) | 2.75 | 3.5 | 5.0 | 3.75 |
| Control | (24 hrs.) | 0.0 | 0.0 | 0.0 | 0.0 |
| A | (48 hrs.) | 5.0 | 4.75 | — | 4.88 |
| B | (48 hrs.) | 4.5 | 5.0 | — | 4.75 |
| Control | (48 hrs.) | 0.5 | 0.5 | — | 0.5 |

EXAMPLES 4–9

In examples 4–9, bait formulations according to the invention were prepared and tested for efficacy as a soil bait against immature corn rootworm beetles (larvae). All baits had the basic formulation shown in Table 3.

TABLE 3

| Component | % by Weight |
| --- | --- |
| Carrageenan gum | 3 |
| 300 Bloom Type A gelatin | 7 |
| Sorbitol plasticizer | 6 |
| Sodium benzoate preservative | 0.1 |
| Cucurbitacin liquid[1] | 10 |
| Corn germ (milled) | 40.6 |

[1]Liquor containing 40 wt % solids (100 g liquor = 2000 ppm Cucurbitacin E)

The specific toxicant for each bait formulation is listed in Table 4. The amount of added clay was adjusted to compensate for differences in the amount and density of toxicant. The amount of clay within the tested amounts was not expected to significantly affect palatability of the bait to the test larvae.

TABLE 4

| Example | Clay (wt %) | Toxicant | Weight % |
| --- | --- | --- | --- |
| 4 | 23.3 | Carbaryl | 10 |
| 5 | 28.3 | Carbaryl | 5 |
| 6 | 28.3 | Chlorpyrifos | 5 |
| 7 | 30.8 | Chlorpyrifos | 2.5 |
| 8 | 29.3 | Phorate | 4 |
| 9 | 31.3 | Phorate | 2 |

Each bait formulation was tested for efficacy by mixing the bait into soil surrounding the roots of living corn plants. Each test was replicated twelve times. An equal number of corn rootworm larvae were introduced into each sample plot. The number of live larvae found in the soil and near the roots was counted at one, four, and six weeks after introduction. Control at the six week period is a measure of the bait's ability to withstand microbial attack. Table 5 reports the results.

TABLE 5

| | Number of Live CRW Larvae (avg.) | | | | | | | | |
| --- | --- | --- | --- | --- | --- | --- | --- | --- | --- |
| | 1 week | | | 4 weeks | | | 6 weeks | | |
| Example | Soil | Roots | Total | Soil | Roots | Total | Soil | Roots | Total |
| Control | 30 | 3 | 33 | 13 | 5 | 18 | 9 | 1 | 10 |
| 4 | 26.7 | 8 | 34.7 | 1.7 | 0 | 1.7 | 6.7 | 1.7 | 8.3 |
| 5 | 17 | 6.3 | 23.3 | 2 | 0 | 2 | 1 | 1.7 | 2.7 |
| 6 | 2.3 | 0.7 | 3 | 0 | 0 | 0 | 0.3 | 0.3 | 0.7 |
| 7 | 1 | 0 | 1 | 0 | 0 | 0 | 0 | 0 | 0 |
| 8 | 1.7 | 0 | 1.7 | 0.3 | 0 | 0.3 | 0 | 0.3 | 0.3 |
| 9 | 5 | 0.3 | 5.3 | 0.3 | 0 | 0.3 | 0 | 0 | 0 |

The examples presented herein are intended to serve as an aid to understanding the present invention. Specific materials and particle sizes exemplified are not intended to serve as a limitation on the scope of the appended claims.

We claim:

1. A bait composition useful for controlling insect populations, said composition consisting essentially of a binder that is palatable to diabroticine insects and is able to bind together bait components yet pass through equipment used to form particles, an insecticide, and a feeding stimulant wherein said binder has homogeneously distributed therein: (a) insecticide in an amount 0.01–99 w % based on the total weight of said bait; and (b) 0.01–99 wt % based on the total weight of said bait of corn germ in an amount sufficient to stimulate feeding in a target insect and less than 25 wt %, based on the weight of said corn germ, of corn endosperm associated therewith.

2. A bait composition as in claim 1 wherein said insecticide is selected from the group consisting of organophosphates, carbamates, bacillus thuringiensis, and diabroticidal viruses.

3. A bait composition according to claim 2 wherein said insecticide is selected from the group consisting of phorate, chlorpyrifos, and carbaryl.

4. A bait as in claim 1 wherein said binder further consists essentially of a plasticizer and a preservative.

5. A bait composition as in claim 1 wherein said bait further consists essentially of a cucurbitacin.

6. A bait as m claim 1 wherein said binder is selected from the group consisting of a hot water soluble polymer, a water soluble polymer, a water swellable polymer, and calcium alginate.

7. A bait as in claim 6 wherein said binder is selected from the group consisting of pork gelatin; beef gelatin; xanthan gum; carrageeenan; guar gum; gellan gum; agar; gum karaya; polyethylene glycol; polyethylene glycol containing zein, shellac, or a fatty acid amide in an amount sufficient to reduce water solubility of the polyethylene glycol; and mixtures thereof.

8. A bait as in claim 1 wherein said binder further consists essentially of a clay.

9. A bait as in claim 1 wherein said bait exhibits the form of a dry granular bait.

10. A bait as in claim 7 wherein said binder consists essentially of polyethylene glycol.

11. A bait as in claim 1 wherein said binder consists essentially of a gelatin.

12. A bait as in claim 1 wherein said bait is intended for spraying and exhibits a diameter of less than about 1000 μm.

13. A bait as in claim 9 wherein said bait exhibits a particle size within the range from about 800 μm to about 2000 μm.

14. The bait as in claim 1 wherein said insecticide and said corn germ are each in the form of particles exhibiting a diameter of less than about 50 μm.

* * * * *